United States Patent
Carvin et al.

(10) Patent No.: US 9,108,121 B2
(45) Date of Patent: Aug. 18, 2015

(54) PLANT FOR THE CRYSTALLIZATION OF ADIPIC ACID

(75) Inventors: Philippe Carvin, Lyons (FR); Fabien Bellenger, Shanghai (CN); Serge Crottier-Combe, Diemoz (FR)

(73) Assignee: RHODIA OPERATIONS, Paris (FR)

( * ) Notice: Subject to any disclaimer, the term of this patent is extended or adjusted under 35 U.S.C. 154(b) by 1085 days.

(21) Appl. No.: 13/132,188

(22) PCT Filed: Nov. 24, 2009

(86) PCT No.: PCT/EP2009/065758
§ 371 (c)(1),
(2), (4) Date: Jul. 29, 2011

(87) PCT Pub. No.: WO2010/063619
PCT Pub. Date: Jun. 10, 2010

(65) Prior Publication Data
US 2011/0274591 A1  Nov. 10, 2011

(30) Foreign Application Priority Data

Dec. 1, 2008  (FR) ...................................... 08 06729

(51) Int. Cl.
*C30B 7/08* (2006.01)
*B01D 9/00* (2006.01)
*C07C 51/43* (2006.01)

(52) U.S. Cl.
CPC ............. *B01D 9/0013* (2013.01); *C07C 51/43* (2013.01)

(58) Field of Classification Search
USPC .................................. 117/200, 201, 900, 68
See application file for complete search history.

(56) References Cited

U.S. PATENT DOCUMENTS

| 3,607,926 A | * | 9/1971 | Smetana | ....................... 562/543 |
| 4,014,903 A | | 3/1977 | Moore | |
| 5,321,157 A | * | 6/1994 | Kollar | ........................... 562/543 |
| 5,695,716 A | | 12/1997 | Kohler et al. | |
| 2004/0005255 A1 | * | 1/2004 | Green | ........................ 422/245.1 |

FOREIGN PATENT DOCUMENTS

| JP | H07-197181 A | 8/1995 |
| JP | 2007-509071 A | 4/2007 |
| WO | 2005-037762 A1 | 4/2005 |

OTHER PUBLICATIONS

Kachanov et al., "Corrosion of Weld Joints in the Manufacture of Adipic Acid," Protection of Metals, Nov. 1981, pp. 599-602, vol. 17, No. 6.
Tsinman et al., "Corrosion of stainless steels in fused dicarboxylic acids," Journal of Applied Chemistry of USSR, Aug. 1965, pp. 1828-1831, vol. 38, No. 8.
Preliminary International Report of Patentability (Form PCT/IB/373) and an English language translation of the Written Opinion of the International Searching Authority (PCT/ISA/237) issued on Jun. 7, 2011, in corresponding International Patent Application No. PCT/EP2009/065758.
International Search Report issued on Apr. 8, 2010, by the European Patent Office as the international Searching Authority in corresponding International Patent Application No. PCT/EP2009/065758.
A M Goldman, Chimicheskaya promyshlennost, Goschimizdat, 1962, vol. 5, pp. 17-21 and English translation thereof.
Uranus® 65, Arcelor Mittal, Industeel, Jun. 3, 2013, pp. 1-4.
Whillock G.O.H. et al., "Techniques for measuring the end-grain corrosion resistance of austenitic stainless steels", Corrosion, Jan. 2005, vol. 61, No. 1, pp. 58-67.
Chlibec G. et al., "Einsatzmöglichkeiten verschiedener Werkstoffe in salpetersäurehaltigen Medien", Thyssen Edelstahl Technische Berichte, 1988, vol. 14, No. 1, pp. 39-48.

* cited by examiner

Primary Examiner — Robert M Kunemund

(57) ABSTRACT

A plant for the crystallization of adipic acid is described. A plant for the crystallization of adipic acid, some parts of which are made of a corrosion-resistant material, is also described. The corrosion-resistant material used can be a reference austenitic stainless steel of AISI 310L type, according to the AISI (USA) nomenclature, or X1 CrNi 25-21 (1.4335) type, according to the European nomenclature.

7 Claims, No Drawings

PLANT FOR THE CRYSTALLIZATION OF ADIPIC ACID

This application is the United States national phase of PCT/EP2009/065758, filed Nov. 24, 2009, and designating the United States (published in the French language on Jun. 10, 2010, as WO 2010/063619 A1; the title and abstract were also published in French), which claims foreign priority under 35 U.S.C. §119 of FR 0806729, filed Dec. 1, 2008, each hereby expressly incorporated by reference in its entirety and each assigned to the assignee hereof.

The present invention relates to a plant for the crystallization of adipic acid.

Adipic acid is an important chemical compound used as starting material in the synthesis of many compounds. Thus, adipic acid is an important intermediate compound in the synthesis of polyamides, more particularly PA 6.6, and in the manufacture of polyesters or polyurethanes. Adipic acid is also used as additive in many other applications, such as the manufacture of plasticizers, for example.

Adipic acid is generally synthesized from cyclohexane by oxidation of the latter to give a cyclohexanone/cyclohexanol mixture, followed by oxidation of this mixture by nitric acid to give adipic acid.

Several processes for the oxidation of cyclohexane to give cyclohexanone/cyclohexanol are carried out with different catalysts.

The oxidation of the cyclohexanol/cyclohexanone mixture with nitric acid is carried out in the presence of a metal catalyst, the adipic acid being generally recovered and purified by successive crystallizations.

Processes for the direct oxidation of cyclohexane by oxygen or air, in the presence of metal catalysts and of a solvent, such as acetic acid, to give adipic acid have also been provided. In these processes, the adipic acid is generally recovered in the form of an aqueous solution.

Whatever the process for the synthesis of the adipic acid, it is necessary, in order to obtain a compound compatible for in particular the uses described above, to purify it. The purification processes generally used employ crystallization stages consisting conventionally in concentrating and/or in cooling the adipic acid solution in order to obtain the formation of pure adipic acid crystals.

These crystallizations are generally carried out in large-sized crystallizers. A crystallization plant can comprise several crystallizers arranged in series or a device comprising several compartments making it possible to carry out continuous purification or several crystallizers operating according to a batchwise process.

The crystallizers are generally equipped with stirring means and means for cooling and/or concentrating the solution. The latter means can be composed of devices brought into contact with the solution and in which a heat-exchange fluid circulates or means making it possible to evaporate the solution, in particular by placing under reduced pressure.

The means for cooling and/or concentrating the solution can comprise several devices used alone or in combination, such as, for example, a jacket in the wall of the crystallizer, components comprising means for circulating a heat-exchange fluid positioned in the solution or an external circuit for circulation of the solution comprising a heat exchanger. This list of means for cooling and/or concentrating the solution is given only by way of indication and does not have a limiting nature.

In order for the crystallizer to operate correctly and in order to maintain its productive output, it is necessary to control certain operating parameters and more particularly the parameters which govern the phenomena of fouling of the crystallizer by deposition of crystalline adipic acid on the walls of the equipment. This phenomenon, known as "fouling", depends on the nature of the material and on the surface condition of the walls. More particularly, it will be promoted by the difference in temperature between the solution and the walls in contact with the solution. This is because, if this difference in temperature is greater than a critical value which is a function of the concentration and of the temperature of the solution, of the flow rate for circulation of the solution in the crystallizer, of the nature of the material and of the surface condition of the wall, deposition of adipic acid which adheres to the wall is produced. The deposition of adipic acid is also observed, independently of the difference in temperature, on the walls whose surface condition has deteriorated, in particular in the case of a crystallization by concentration of the solution obtained by placing the crystallizer under reduced pressure.

In order to regain acceptable operating conditions for the crystallizer, it is necessary to periodically shut down the process in order to remove the deposits of adipic acid on the walls of the heat exchanger or the walls of the crystallizer.

Furthermore, untimely detachment of this deposit during an operation for the production of adipic acid can result in mechanical damage or indeed even can result in the fluctuation in the quality of the adipic acid produced.

In order to limit this fouling phenomenon, the internal walls of the crystallizer and the walls of the device for cooling and/or concentrating the solution are polished in order to obtain a surface condition with a minimal roughness. These polished surfaces can also be cleaned and washed by conventional cleaning techniques used in the field of the treatment of metal surfaces.

However, the surface condition of the walls can rapidly deteriorate under the effect of chemical corrosion, in particular when the crystallization of the adipic acid is carried out starting from the solutions obtained during the oxidation of cyclohexanone/cyclohexanol mixtures by nitric acid. This is because these solutions are acidic and comprise a large amount of nitric acid and/or nitrate ions.

In order to limit the phenomenon of fouling and optionally the deterioration in the surface condition, the crystallizers and the walls of the exchange devices are often made of austenitic stainless steel of AISI 304L type. However, these phenomena of fouling and corrosion are still found. The use of this type of material does not make it possible to stop or reduce shutdowns of the plant in order to remove the fouling.

There thus still exists a need to provide materials or devices which make it possible to retain a correct surface condition and to limit the effects of corrosion in order to reduce and stop this phenomenon of fouling.

The present invention provides, in order to overcome this problem, for the use, in the manufacture of the walls in contact with the adipic acid solution, of a material chosen from specific grades of stainless steel.

To this end, the invention provides a plant or a crystallizer for the crystallization of adipic acid comprising a vessel or a crystallizer, means for stirring and means for cooling and/or concentrating the adipic acid solution, characterized in that at least a part of the walls in contact with the adipic acid solution and forming part of the vessel or crystallizer and/or of the means for concentrating and/or cooling the solution is made of austenitic stainless steel of AISI 310L type according to the AISI (USA) nomenclature.

The austenitic stainless steel of AISI 310L type is also denoted X1 CrNi 25-21 (1.4335) according to the European nomenclature.

According to one characteristic of the invention, the means for cooling and/or concentrating the adipic acid solution are composed of devices in contact with the solution. More particularly, devices comprising circulation of heat-exchange fluid can advantageously be used to cool the solution. According to the invention, the walls of these cooling devices in contact with the adipic acid solution are made of austenitic stainless steel of AISI 310L type. In another embodiment of the process for crystallization of adipic acid with concentration of the solution by evaporation obtained by placing the plant under reduced pressure, the parts of the plant, such as the internal walls of the crystallizer, for example, are made of austenitic stainless steel of AISI 310L type.

According to another characteristic of the invention, the surfaces or walls made of austenitic stainless steel of AISI 310L type are subjected to a polishing operation before they are installed in the crystallizer. This polishing can be carried out by any known means employing physical and/or chemical processes in order to reduce the roughness of the surface.

By way of indication and without a limiting nature, it is advantageous for the roughness of the surface to be less than 0.3 µm, measured according to the method defined by Standards NF EN ISO 3274 and NF EN ISO 4288.

The means for cooling and/or concentrating the adipic acid solution can be of varied form, such as coils, double-walled plates comprising circulation of fluids, or the like.

The crystallizer of the invention is suitable in particular for crystallizing adipic acid starting from the solutions obtained at the outlet of the stage of oxidation of the cyclohexanone/cyclohexanol mixture by nitric acid.

The invention will be better illustrated in the light of the examples given below solely by way of indication.

Tests for determining the resistance to corrosion and the change in the surface condition of items made of different grades of stainless steels were carried out according to the procedure below:

Test specimens of parallelepipedal shape with dimensions of 50×30 mm, the surface of which was polished in order to have an initial roughness Ra of less than 0.1 µm, were immersed in a medium resulting from the oxidation of a cyclohexanone/cyclohexanol mixture by nitric acid comprising a concentration by weight of adipic acid of 24% and a content of nitric acid of the order of 28% by weight.

The solution is maintained at a temperature of 90° C. at atmospheric pressure and is stirred throughout the duration of immersion. After immersing for 400 hours, the surface condition of the test specimens and the loss in thickness are determined. These test specimens are again immersed in the same medium for a further duration of 400 hours. However, the solution is replaced before each further immersion.

The test specimens tested were made of two grades of stainless steel:

Test specimen 1: steel of AISI 304L type
Test specimen 2: steel of AISI 310L type The compositions of these grades of steel are given in Table I below:

| Metal composition | 304 L | 310 L |
|---|---|---|
| | % by weight | |
| C | 0.015 | 0.017 |
| S | 0.002 | 0.006 |
| P | 0.025 | 0.019 |
| Si | 0.248 | 0.14 |
| Mn | 1.690 | 0.593 |
| Cr | 18.410 | 24.29 |
| Ni | 10.480 | 21.62 |
| Mo | 0.125 | 0.317 |
| Cu | 0.069 | 0.167 |
| N | — | — |
| Fe | bal. | bal. |

(bal. means remainder to 100%)

The results observed are collated in Table II below:

| Test specimen | | 1 | 2 |
|---|---|---|---|
| Initial | Roughness Ra (µm) | <0.1 | <0.1 |
| | Loss in thickness (µm/year) | 0 | 0 |
| 400 hours | Roughness Ra (µm) | 0.5 | <0.1 |
| | Loss in thickness (µm/year) | 90 | <5 |
| 800 hours | Roughness Ra (µm) | 1.9 | 0.2 |
| | Loss in thickness (µm/year) | 130 | <20 |
| 1200 hours | Roughness Ra (µm) | 2.8 | 0.2 |
| | Loss in thickness (µm/year) | 130 | <5 |
| 1600 hours | Roughness Ra (µm) | 4.1 | 0.3 |
| | Loss in thickness (µm/year) | 230 | <20 |
| 2000 hours | Roughness Ra (µm) | 4.7 | 0.3 |
| | Loss in thickness (µm/year) | 90 | <5 |
| 2400 hours | Roughness Ra (µm) | 4.7 | 0.3 |
| | Loss in thickness (µm/year) | 140 | <5 |

It emerges from the above results that, for the test specimen 2, which corresponds to the present invention, there is a slight variation of the roughness upon time compared to the test specimen measured for a AISI 304L type (test specimen 1). This feature shows the fact that the use of a steel of AISI 310L type according to the invention allows to maintain a good surface condition upon time for the concerned reaction and thus to limit the phenomenon of fouling as much as possible.

Moreover, the above results show that the resistance to corrosion (loss in thickness) of a steel of AISI 310L type in a medium resulting from the oxidation of a cyclohexanone/cyclohexanol mixture by nitric acid (according to the invention) is increased.

The invention claimed is:

1. A plant for crystallization of adipic acid, the plant comprising a crystallization vessel equipped with a means for stirring and a means for cooling and/or concentrating an adipic acid solution, wherein at least a part of the crystallization vessel's walls and/or of the means for cooling and/or concentrating that comes into contact with the adipic acid solution is made of austenitic stainless steel AISI 310L material, according to AISI (USA) nomenclature.

2. The plant according to claim 1, wherein the adipic acid solution is obtained by oxidation of a cyclohexanone/cyclohexanol mixture by nitric acid.

3. The plant according to claim 1, wherein the plant comprises a device for cooling the solution comprising circulation of a heat-exchange fluid, wherein the device is made of austenitic stainless steel AISI 310L material.

4. The plant according to claim 1, wherein at least a part of the internal walls of the crystallization vessel is made of austenitic stainless steel AISI 310L material.

5. The plant according to claim 1, wherein a concentration of the solution is obtained by placing the crystallization vessel under reduced pressure.

6. A plant according to claim 3, wherein a surface of the was of the device made of austenitic stainless steel AISI 310L material is polished.

7. The plant according to claim 6, wherein the polished surface made of austenitic stainless steel AISI 310L material exhibits a roughness of less than 0.3 μm, measured according to a method defined by Standards NF EN ISO 3274 and NF EN ISO 4288.

\* \* \* \* \*